(12) United States Patent
Tamarkin et al.

(10) Patent No.: US 7,645,803 B2
(45) Date of Patent: *Jan. 12, 2010

(54) SACCHARIDE FOAMABLE COMPOSITIONS

(75) Inventors: Dov Tamarkin, Maccabim (IL); Doron Friedman, Karmei Yosef (IL); Alex Besonov, Rehovot (IL)

(73) Assignee: Foamix Ltd., Ness Ziona (IL)

( * ) Notice: Subject to any disclaimer, the term of this patent is extended or adjusted under 35 U.S.C. 154(b) by 182 days.

This patent is subject to a terminal disclaimer.

(21) Appl. No.: 11/430,437

(22) Filed: May 9, 2006

(65) Prior Publication Data

US 2006/0275221 A1    Dec. 7, 2006

Related U.S. Application Data

(60) Provisional application No. 60/679,020, filed on May 9, 2005, provisional application No. 60/784,793, filed on Mar. 21, 2006.

(51) Int. Cl.
| | |
|---|---|
| *A61K 9/12* | (2006.01) |
| *A61K 8/02* | (2006.01) |
| *A61K 31/70* | (2006.01) |
| *A61K 31/715* | (2006.01) |
| *A01N 25/02* | (2006.01) |
| *A01N 43/04* | (2006.01) |

(52) U.S. Cl. .................. 514/945; 424/43; 424/401; 514/23; 514/53; 514/54

(58) Field of Classification Search .............. None
See application file for complete search history.

(56) References Cited

U.S. PATENT DOCUMENTS

| | | | |
|---|---|---|---|
| 3,178,352 A | 4/1965 | Erickson | |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienciewicz | |
| 3,263,869 A | 8/1966 | Corsette | |
| 3,303,970 A | 2/1967 | Breslau et al. | |
| 3,366,494 A | 1/1968 | Bower | |
| 3,369,034 A | 2/1968 | Chalmers | |
| 3,419,658 A | 12/1968 | Amsdon | |
| 3,559,890 A | 2/1971 | Brooks et al. | |
| 3,561,262 A | 2/1971 | Borocki | |
| 3,577,518 A | 5/1971 | Shepherd | |
| 3,770,648 A | 11/1973 | Mackes | |
| 3,787,566 A | 1/1974 | Gauvreau | |
| 3,882,228 A | 5/1975 | Boncey et al. | |
| 3,886,084 A | 5/1975 | Vassiliades | |
| 3,912,665 A | 10/1975 | Spitzer et al. | |
| 3,923,970 A | 12/1975 | Breuer | |
| 3,929,985 A | 12/1975 | Webb, Jr. | |
| 3,966,090 A | 6/1976 | Prussin et al. | |
| 3,970,584 A * | 7/1976 | Hart et al. ................. 516/10 |
| 3,993,224 A | 11/1976 | Harrison | |
| 4,124,149 A | 11/1978 | Spitzer et al. | |
| 4,145,411 A | 3/1979 | Mende | |
| 4,160,827 A | 7/1979 | Cho et al. | |
| 4,213,979 A | 7/1980 | Levine | |
| 4,214,000 A | 7/1980 | Papa | |
| 4,252,787 A | 2/1981 | Sherman et al. | |
| 4,254,104 A | 3/1981 | Suzuki | |
| 4,268,499 A | 5/1981 | Keil | |
| 4,271,149 A | 6/1981 | Winicov et al. | |
| 4,385,161 A | 5/1983 | Caunt et al. | |
| 4,522,948 A | 6/1985 | Walker | |
| 4,529,601 A | 7/1985 | Broberg et al. | |
| 4,529,605 A | 7/1985 | Lynch et al. | |
| 4,576,961 A | 3/1986 | Lorck et al. | |
| 4,627,973 A | 12/1986 | Moran | |
| 4,628,063 A | 12/1986 | Haines et al. | |
| 4,752,465 A | 6/1988 | Mackles | |
| 4,784,842 A | 11/1988 | London et al. | |
| 4,792,062 A | 12/1988 | Goncalves et al. | |
| 4,808,388 A | 2/1989 | Beutler et al. | |
| 4,822,613 A | 4/1989 | Rodero | |
| 4,827,378 A | 5/1989 | Gillan et al. | |
| 4,837,378 A | 6/1989 | Borgman | |
| 4,863,900 A | 9/1989 | Pollock et al. | |
| 4,874,794 A | 10/1989 | Katz | |
| 4,885,282 A | 12/1989 | Thornfeldt | |
| 4,913,893 A | 4/1990 | Varco | |
| 4,957,732 A | 9/1990 | Grollier et al. | |
| 4,963,351 A | 10/1990 | Weston | |
| 4,981,677 A | 1/1991 | Thau | |
| 4,992,478 A | 2/1991 | Geria | |
| 5,002,680 A | 3/1991 | Schmidt et al. | |
| 5,007,556 A | 4/1991 | Lover | |
| 5,034,220 A | 7/1991 | Helioff et al. | |
| 5,053,228 A | 10/1991 | Mori et al. | |
| 5,071,648 A | 12/1991 | Rosenblatt | |
| 5,089,252 A | 2/1992 | Grollier | |

(Continued)

FOREIGN PATENT DOCUMENTS

DE    10138495    2/2003

(Continued)

OTHER PUBLICATIONS

Molan (World Wide Wounds Dec. 2001 pp. 1-13).*

(Continued)

*Primary Examiner*—Ernst V Arnold
(74) *Attorney, Agent, or Firm*—Wilmer Cutler Pickering Hale and Dorr LLP

(57) ABSTRACT

A foamable composition, containing a saccharide for use in the treatment of various disorders including: water, a saccharide, about 0.2% to about 5% by weight of a surface-active agent, about 0.01% to about 5% by weight of at least one polymeric agent selected from a bio-adhesive agent, a gelling agent, a film forming agent and a phase change agent, and a liquefied or compressed gas propellant at a concentration of about 3% to about 25% by weight of the total composition.

28 Claims, No Drawings

U.S. PATENT DOCUMENTS

| | | |
|---|---|---|
| 5,094,853 A | 3/1992 | Hagarty |
| 5,100,917 A | 3/1992 | Flynn et al. |
| 5,130,121 A | 7/1992 | Kopolow et al. |
| 5,135,915 A | 8/1992 | Czarniecki et al. |
| 5,143,717 A | 9/1992 | Davis |
| 5,156,765 A | 10/1992 | Smrt |
| 5,164,357 A | 11/1992 | Bartman et al. |
| 5,167,950 A | 12/1992 | Linds |
| 5,171,577 A | 12/1992 | Griat et al. |
| 5,204,093 A | 4/1993 | Victor |
| 5,208,031 A | 5/1993 | Kelly |
| 5,217,707 A | 6/1993 | Szabo |
| 5,230,897 A | 7/1993 | Griffin et al. |
| 5,254,334 A | 10/1993 | Ramirez et al. |
| 5,262,407 A | 11/1993 | Leveque et al. |
| 5,279,819 A | 1/1994 | Hayes |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,326,557 A | 7/1994 | Glover et al. |
| 5,352,437 A | 10/1994 | Nakagawa |
| 5,380,761 A | 1/1995 | Szabo |
| 5,384,308 A | 1/1995 | Henkin |
| 5,411,992 A | 5/1995 | Eini et al. |
| 5,422,361 A | 6/1995 | Munayyer et al. |
| 5,429,815 A | 7/1995 | Faryniarz |
| 5,435,996 A | 7/1995 | Glover et al. |
| 5,491,245 A | 2/1996 | Gruning et al. |
| 5,529,770 A | 6/1996 | McKinzie et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,578,315 A | 11/1996 | Chien et al. |
| 5,589,515 A | 12/1996 | Suzuki et al. |
| 5,603,940 A | 2/1997 | Candau et al. |
| 5,614,171 A | 3/1997 | Clavenna et al. |
| 5,635,469 A | 6/1997 | Fowler et al. |
| 5,641,480 A | 6/1997 | Vermeer |
| 5,650,554 A | 7/1997 | Moloney |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,700,396 A | 12/1997 | Suzuki et al. |
| 5,716,611 A | 2/1998 | Oshlack et al. |
| 5,719,197 A | 2/1998 | Kanios |
| 5,730,964 A | 3/1998 | Waldstreicher |
| 5,733,558 A | 3/1998 | Breton et al. |
| 5,753,245 A | 5/1998 | Fowler et al. |
| 5,759,520 A | 6/1998 | Sachetto |
| 5,759,579 A | 6/1998 | Singh et al. |
| 5,783,202 A | 7/1998 | Tomlinson et al. |
| 5,792,922 A | 8/1998 | Moloney |
| 5,817,322 A | 10/1998 | Xu |
| 5,824,650 A | 10/1998 | De Lacharriere et al. |
| 5,833,960 A | 11/1998 | Gers-Barlag et al. |
| 5,840,744 A | 11/1998 | Borgman |
| 5,856,452 A | 1/1999 | Moloney et al. |
| 5,871,720 A | 2/1999 | Gutierrez |
| 5,877,216 A | 3/1999 | Place |
| 5,879,469 A | 3/1999 | Avram et al. |
| 5,885,581 A | 3/1999 | Massand |
| 5,889,028 A | 3/1999 | Sandborn |
| 5,902,574 A | 5/1999 | Stoner et al. |
| 5,902,789 A | 5/1999 | Stoltz |
| 5,911,981 A | 6/1999 | Dahms |
| 5,922,331 A | 7/1999 | Mausner |
| 5,948,682 A | 9/1999 | Moloney |
| 5,951,993 A | 9/1999 | Scholz et al. |
| 5,952,392 A | 9/1999 | Katz |
| 5,961,957 A | 10/1999 | McAnalley |
| 5,972,310 A | 10/1999 | Sachetto |
| 5,993,846 A | 11/1999 | Friedman et al. |
| 6,019,967 A | 2/2000 | Breton et al. |
| 6,033,647 A | 3/2000 | Touzan et al. |
| 6,042,848 A | 3/2000 | Lawyer et al. |
| 6,071,536 A | 6/2000 | Suzuki |
| 6,080,394 A | 6/2000 | Lin |
| 6,087,317 A | 7/2000 | Gee |
| 6,093,408 A | 7/2000 | Hasenoehrl et al. |
| 6,113,888 A | 9/2000 | Castro et al. |
| 6,121,210 A | 9/2000 | Taylor |
| 6,126,920 A | 10/2000 | Jones et al. |
| 6,140,355 A | 10/2000 | Egidio |
| 6,146,645 A | 11/2000 | Deckers et al. |
| 6,183,762 B1 | 2/2001 | Deckers et al. |
| 6,186,367 B1 | 2/2001 | Harrold |
| 6,187,290 B1 | 2/2001 | Gilchrist et al. |
| 6,210,742 B1 | 4/2001 | Deckers et al. |
| 6,221,381 B1 | 4/2001 | Shelford et al. |
| 6,224,888 B1 | 5/2001 | Vatter |
| 6,251,369 B1 | 6/2001 | Stoltz |
| 6,258,374 B1 | 7/2001 | Friess et al. |
| 6,271,295 B1 | 8/2001 | Powell |
| 6,287,546 B1 | 9/2001 | Reich et al. |
| 6,294,550 B1 | 9/2001 | Place |
| 6,306,841 B1 | 10/2001 | Place |
| 6,333,362 B1 | 12/2001 | Lorant |
| 6,358,541 B1 | 3/2002 | Goodman |
| 6,372,234 B1 | 4/2002 | Deckers et al. |
| 6,383,471 B1 | 5/2002 | Chen et al. |
| 6,395,300 B1 | 5/2002 | Straub et al. |
| 6,410,036 B1 | 6/2002 | De Rosa et al. |
| 6,423,323 B2 | 7/2002 | Neubourg |
| 6,433,033 B1 | 8/2002 | Isobe et al. |
| 6,437,006 B1 | 8/2002 | Yoon |
| 6,468,989 B1 | 10/2002 | Chang et al. |
| 6,524,594 B1 | 2/2003 | Santora et al. |
| 6,536,629 B2 | 3/2003 | van der Heijden |
| 6,544,530 B1 | 4/2003 | Friedman |
| 6,548,074 B1 | 4/2003 | Mohammadi |
| 6,582,710 B2 | 6/2003 | Deckers et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,649,571 B1 | 11/2003 | Morgan |
| 6,672,483 B1 | 1/2004 | Roy et al. |
| 6,730,288 B1 | 5/2004 | Abram |
| 6,753,167 B2 | 6/2004 | Moloney et al. |
| 6,765,001 B2 | 7/2004 | Gans et al. |
| 6,777,591 B1 | 8/2004 | Chaudhary |
| 6,946,120 B2 | 9/2005 | Wai-Chiu So et al. |
| 7,029,659 B2 | 4/2006 | Abram et al. |
| 7,137,536 B2 | 11/2006 | Walters et al. |
| 2002/0032171 A1 | 3/2002 | Chen et al. |
| 2002/0035046 A1 | 3/2002 | Lukenbach et al. |
| 2002/0045659 A1 | 4/2002 | Michelet et al. |
| 2002/0048798 A1 | 4/2002 | Avery et al. |
| 2002/0072544 A1 | 6/2002 | Miller et al. |
| 2002/0098215 A1 | 7/2002 | Douin et al. |
| 2004/0018228 A1 | 1/2004 | Fischell et al. |
| 2004/0053797 A1 | 3/2004 | Chen et al. |
| 2004/0063787 A1 | 4/2004 | Villanueva |
| 2004/0151671 A1 | 8/2004 | Abram et al. |
| 2004/0192754 A1 | 9/2004 | Shapira et al. |
| 2004/0234475 A1 | 11/2004 | Lannibois-Drean |
| 2004/0241099 A1 | 12/2004 | Popp et al. |
| 2004/0265240 A1 | 12/2004 | Tamarkin et al. |
| 2005/0031547 A1 | 2/2005 | Tamarkin et al. |
| 2005/0054991 A1 | 3/2005 | Tobyn et al. |

| | | |
|---|---|---|
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0186142 A1 | 8/2005 | Tamarkin et al. |
| 2005/0186147 A1 | 8/2005 | Tamarkin et al. |
| 2005/0196414 A1 | 9/2005 | Dake et al. |
| 2005/0205086 A1 | 9/2005 | Tamarkin et al. |
| 2005/0232869 A1 | 10/2005 | Tamarkin et al. |
| 2005/0244342 A1 | 11/2005 | Friedman et al. |
| 2005/0255048 A1 | 11/2005 | Hirsh |
| 2005/0271596 A1 | 12/2005 | Friedman et al. |
| 2005/0271598 A1 | 12/2005 | Friedman et al. |
| 2005/0281755 A1 | 12/2005 | Zarif et al. |
| 2006/0018937 A1 | 1/2006 | Friedman et al. |
| 2006/0018938 A1 | 1/2006 | Neubourg |
| 2006/0193789 A1 | 8/2006 | Tamarkin et al. |
| 2006/0233721 A1 | 10/2006 | Tamarkin et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2007/0020213 A1 | 1/2007 | Tamarkin et al. |
| 2007/0059253 A1 | 3/2007 | Popp et al. |
| 2007/0069046 A1 | 3/2007 | Eini et al. |
| 2007/0253911 A1 | 11/2007 | Tamarkin et al. |
| 2007/0280891 A1 | 12/2007 | Tamarkin et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/031907 A1 | 2/2008 | Tamarkin et al. |
| 2008/0035155 A1 | 2/2008 | Dahl |
| 2008/0166303 A1 | 7/2008 | Tamarkin et al. |
| 2008/0253973 A1 | 10/2008 | Tamarkin et al. |
| 2008/0317679 A1 | 12/2008 | Tamarkin et al. |

FOREIGN PATENT DOCUMENTS

| | | |
|---|---|---|
| EP | 0156507 | 10/1985 |
| EP | 0186453 | 7/1986 |
| EP | 0270316 | 6/1988 |
| EP | 0488089 A1 | 6/1992 |
| EP | 0535327 | 4/1993 |
| EP | 0598412 | 11/1993 |
| EP | 0738516 | 10/1996 |
| EP | 0979654 A1 | 2/2000 |
| EP | 1055425 A2 | 11/2000 |
| EP | 1 287 813 | 3/2003 |
| EP | 1 428 521 | 6/2004 |
| EP | 1500385 | 1/2005 |
| FR | 2774595 A | 8/1999 |
| FR | 2915891 | 11/2008 |
| GB | 808105 | 1/1959 |
| GB | 922930 | 4/1963 |
| GB | 1121358 | 7/1968 |
| GB | 2166651 | 5/1996 |
| IL | 0152486 | 5/2003 |
| JP | 02184614 | 7/1990 |
| JP | 2008040899 | 2/1996 |
| JP | 2002012513 | 1/2002 |
| WO | WO-89/06537 | 7/1989 |
| WO | WO-92/00077 | 6/1991 |
| WO | WO-91/11991 | 8/1991 |
| WO | WO-96/03115 | 2/1996 |
| WO | WO-96/19921 | 7/1996 |
| WO | WO-96/024325 | 8/1996 |
| WO | WO-96/27376 | 9/1996 |
| WO | WO-97/39745 | 10/1997 |
| WO | WO-98/18472 | 5/1998 |
| WO | WO98/19654 | 5/1998 |
| WO | WO-98/21955 | 5/1998 |
| WO | WO-98/23291 | 6/1998 |
| WO | WO-99/08649 | 2/1999 |
| WO | WO-99/20250 | 4/1999 |
| WO | WO-00/09082 | 2/2000 |
| WO | WO-00/15193 | 3/2000 |
| WO | WO-00/61076 | 10/2000 |
| WO | WO-00/76461 | 12/2000 |
| WO | WO-01/70242 A2 | 9/2001 |
| WO | WO-01/82880 | 11/2001 |
| WO | WO-02/00820 | 1/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | WO-03/000223 | 1/2003 |
| WO | WO-03/051294 | 6/2003 |
| WO | WO-03/053292 | 7/2003 |
| WO | WO-03/055445 | 7/2003 |
| WO | WO-03/075851 | 9/2003 |
| WO | WO-2004/037225 | 5/2004 |
| WO | WO-2004/064833 | 8/2004 |
| WO | WO-2004/071479 A1 | 8/2004 |
| WO | WO-2004/112780 | 12/2004 |
| WO | WO-2005/011567 A2 | 2/2005 |
| WO | WO-2005/018530 A2 | 3/2005 |
| WO | WO-2005/076697 | 8/2005 |
| WO | WO-2005/097068 A1 | 10/2005 |
| WO | WO-2005/102539 | 11/2005 |
| WO | WO-2005/117813 | 12/2005 |
| WO | WO-2006/003481 A2 | 1/2006 |
| WO | WO-2006/010589 | 2/2006 |
| WO | WO-2006/020682 | 11/2006 |
| WO | WO-2006/129161 | 12/2006 |
| WO | WO-2006/131784 | 12/2006 |
| WO | WO-2007/039825 | 4/2007 |
| WO | WO-2007/054818 | 5/2007 |
| WO | WO-2007/085899 | 8/2007 |
| WO | WO-2007/099396 | 9/2007 |
| WO | WO-2008/008397 | 1/2008 |
| WO | WO-2008/075207 | 6/2008 |

OTHER PUBLICATIONS

Barry, B.W. et al, Comparative bio-availability and activity of proprietary topical corticosteroid preparations: vasoconstrictor assays on thirty-one ointments, British Journal of Dermatology, 93, 563-571, 1975.

Martindale, The extra pharmacopoeia [28th] editions, Eds.: Reynolds, J.E.F. and Prasad, A.B., The Pharmaceutical Press, London, pp. 862-864, 1982.

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

International Search Report from PCT/IB2006/003268, mailed Dec. 7, 2007.

Material Safety Data Sheet, Science Lab.com, Polyethylene Glycol 1000, MSDS, Nov. 6, 2008, 6 pages.

D.W.A. Sharp Dictionary of Chemistry, Penguin Books, 1983, 3 pages.

Morgan, Timothy M., et al., "Enhanced Skin Permeation of Sex Hormones with Novel Topical Spray Vehicles," Journal of Pharmaceutical Sciences, vol. 87, 10, Oct. 1998, pp. 1213-1218.

Material Safety Data Sheet, Progesterone, Apr. 26, 2006, 5 pages.

"Licking Vaginal Dryness Without a Prescription," Estronaut, Dec. 14, 2008, 3 pages.

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Gill, A.M, et al., "Adverse Drug Reactions in a Paediatric Intensive Care Unit," Acta Paediatr 84:438-441, 1995.

Gschnait, F., et al., "Topical Indomethacin Protects from UVB and UVA Irradiation," Arch. Dermatol. Res. 276:131-132, 1984.

Hall, Karla, "Diaper Area Hemangiomas: A Unique Set of Concerns," http://members.tripod.com/~Michelle_G/diaper.html, Dec. 1, 2008, 8 pages.

Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.

Galligan, John et al., "Adhesive Polyurethane Liners for Anterior Restorations," J. Dent. Res., Jul.-Aug. 1968, pp. 629-632.

International Search Report and Written Opinion, International Application No. PCT/IB2006/003628, Foamix Ltd., Dec. 7, 2007, 15 pages.

Fonatana, Anthony J., "Water Activity: Why It is Important for Food Safety," International Conference on Food Safety, Nov. 16-18, 1998, pp. 177-185.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Koerber S., "Humectants and Water Activity,", Water Activity News, Issue No. 1083-3943, 2000, 8 pages.

Third Party Submission for U.S. Appl. No. 12/014,088, filed Feb. 4, 2009, 4 pages.

European Official Action, European Patent Application No. 06831721.3, Feb. 3, 2009, 9 pages.

\* cited by examiner

SACCHARIDE FOAMABLE COMPOSITIONS

CROSS-REFERENCE TO RELATED APPLICATION

This application claims the benefit under 35 U.S.C. § 119(e) of U.S. Provisional Patent Application No. 60/679,020, filed on May 9, 2005, entitled Hygroscopic Anti-Infective Compositions, which is herein incorporated by reference in its entirety.

This application claims the benefit under 35 U.S.C. § 119(e) of U.S. Provisional Patent Application No. 60/784,793, filed on Mar. 21, 2006, entitled Polyol Foamable Vehicle and Pharmaceutical Compositions Thereof, which is herein incorporated by reference in its entirety.

BACKGROUND OF THE INVENTION

This invention relates to foamable pharmaceutical and cosmetic compositions.

External topical administration is an important route for the administration of drugs in disease treatment. Many groups of drugs, including, for example, antibiotic, anti-fungal, anti-inflammatory, anesthetic, analgesic, anti-allergic, corticosteroid, retinoid and anti-proliferative medications are generally administered in semisolid preparations. While semi-solid compositions, such as cream and ointment are commonly used by consumers, new forms are desirable in order to achieve better control of the application, while maintaining or bestowing the skin beneficial properties of such products.

There remains an unmet need for improved, easy to use, stable and non-irritating foam formulations, intended for treatment of dermal and mucosal tissues, with unique therapeutic properties.

SUMMARY OF THE INVENTION

The present invention is geared towards providing an improved external topical administration tool.

According to the present invention there is provided a foamable saccharide composition including: (i) water, (ii) a saccharide, (iii) about 0.2% to about 5% by weight of a surface-active agent, (iv) about 0.01% to about 5% by weight of at least one polymeric agent selected from a bio-adhesive agent, a gelling agent, a film forming agent and a phase change agent, and (v) a liquefied or compressed gas propellant at a concentration of about 3% to about 25% by weight of the total composition.

According to further embodiments of the present invention, the saccharide is selected from the group consisting of a saccharide, a monosaccharide, a disaccharide, an oligosaccharide and a sugar alcohol; and naturally occurring saccharide mixtures, such as honey.

According to still further embodiments of the present invention, the saccharide composition further including a foam adjuvant, selected from the group of a long chain fatty alcohol and a long chain fatty acid.

According to yet further embodiments of the present invention, the saccharide composition further includes a hydrophobic solvent.

According to still further embodiments of the present invention, the composition is in the form of an oil in water emulsion; and wherein the HLB of surface-active agent is between about 9 and about 14.

According to further embodiments of the present invention, the saccharide composition further including at least one component, selected from the group consisting of a keratolytic agent, and a polar solvent.

According to still further embodiments of the present invention, the saccharide composition further containing at least one active agent, selected from the group of: an active herbal extract, an acaricide, an age spot and keratose removing agent, an allergen, an analgesic agent, a local anesthetic, an antiacne agent, an antiallergic agent, an antiaging agent, an antibacterial agent, an antibiotic agent, an antiburn agent, an anticancer agent, an antidandruff agent, an antidepressant, an antidermatitis agent, an antiedemic agent, an antihistamine, an antihyperkeratolyte agent, an antiinflammatory agent, an antiirritant, an antilipemic agent, an antimicrobial agent, an antimycotic agent, an antiproliferative agent, an antioxidant, an anti-wrinkle agent, an antipruritic agent, an antipsoriatic agent, an antirosacea agent, an antiseborrheic agent, an antiseptic agent, an antiswelling agent, an antiviral agent, an antiyeast agent, an astringent, a topical cardiovascular agent, a chemotherapeutic agent, a corticosteroid, a dicarboxylic acid, a disinfectant, a fungicide, a hair growth regulator, a hormone, a hydroxy acid, an immunosuppressant, an immunoregulating agent, an insecticide, an insect repellent, a keratolytic agent, a lactam, a metal, a metal oxide, a mitocide, a neuropeptide, a non-steroidal anti-inflammatory agent, an oxidizing agent, a pediculicide, a photodynamic therapy agent, a retinoid, a scabicide, a self tanning agent, a skin whitening agent, a vasoconstrictor, a vasodilator, a vitamin, a vitamin D derivative, a wound healing agent and a wart remover.

According to yet further embodiments of the present invention, the saccharide composition is hygroscopic.

According to still further embodiments of the present invention, the concentration of the saccharide is adjusted to provide a Aw value of the foamable composition selected from the ranges of (1) about 0.8 and about 0.9; (2) about 0.7 and about 0.8; and (3) less than about 0.7.

According to further embodiments of the present invention, the hygroscopic pharmaceutical composition further includes a therapeutically effective concentration of an anti-infective agent According to still further embodiments of the present invention, the anti-infective agent, selected from the group of an antibiotic agent, an antibacterial agent, an antifungal agent, an agent that controls yeast, an antiviral agent and an antiparasitic agent.

According to yet further embodiments of the present invention, the antibiotic agent is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide, a naturally occurring antibiotic compound and analogs, derivatives, salts, ions and complexes thereof.

According to still further embodiments of the present invention, the antifungal agent is useful in the treatment of an infection of dermatophytosis, microsporum, trichophyton and epidermophyton infections, candidiasis, oral candidiasis (thrush), yeast and candida.

According to still further embodiments of the present invention, the antifungal agent is selected from the group consisting of a polyene, natamycin, nystatin; an allylamine, naftifine, terbinafine; an imidazole, bifonazole, clotrimazole, econazole, fenticonazole, ketocanazole, miconazole, oxiconazole; a diazole, a triazoles, fluconazole, itraconazole, terconazole, tolnaftate, ciclopirox, undecylenic acid, sulbentine, griseofulvin, Amphotericin B, flucytosine (5FC), a morpholine compound, amorolfine, and the related morpholines and analogs, derivatives and salts thereof, and any combination thereof at a therapeutically effective concentration. According to a second embodiment of the present invention, there is provided a method of treatment of a disorder of the skin, a body surface, a body cavity or mucosal surface, the nasal cavity, the mouth, the eye, the ear canal, the vagina and the rectum, consisting of administering the saccharide compositions to a target site of treatment.

DETAILED DESCRIPTION OF THE INVENTION

The present invention relates to a foamable composition, containing a saccharide for use in the treatment of various disorders.

According to one or more embodiments of the present invention, the foamable saccharide composition includes:
a. a saccharide aqueous solution;
b. about 0.2% to about 5% by weight of a surface-active agent;
c. about 0.01% to about 5% by weight of at least one polymeric agent; and
d. a liquefied or compressed gas propellant at a concentration of about 3% to about 25% by weight of the total composition.

All % values are provided on a weight (w/w) basis.

Water and optional ingredients are added to complete the total mass to 100%.

Upon release from an aerosol container, the foamable composition forms an expanded foam suitable for the treatment of an infected surface and for topical administration to the skin, a body surface, a body cavity or a mucosal surface.

Saccharide

Saccharides vary from simple sugars containing from three to seven carbon atoms to very complex polymers.

Exemplary saccharides include, but are not limited to monosaccharide, disaccharides, oligosaccharides and sugar alcohols, which possess hygroscopic properties.

A monosaccharide is a simple sugar that cannot be hydrolysed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol).

In an embodiment of the present invention, the concentration of the saccharide in the foamable composition of the present invention is between about 20% and about 80%. In certain embodiments, the concentration of the saccharide is between about 50% and about 80%. An exemplary saccharide solution, suitable according to the present invention contains 70% sorbitol in water. Another example is honey, which is composed primarily of sugars and water. The average honey contains about 80% saccharides and about 17% water, and the primary saccharides are fructose and glucose.

Polymeric Agent

The composition of the present invention contains a polymeric agent. It has been documented that the presence of a polymeric agent is desirable for the creation of foam, having fine bubble structure, which does not readily collapse upon release from the pressurized aerosol can. The polymeric agent serves to stabilize the foam composition and to control drug residence in the target organ. Preferably, the polymeric agent is selected from the group consisting of a bioadhesive agent, a gelling agent, a film forming agent and a phase change agent.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Further exemplary gelling agents include the acrylic acid/ethyl acrylate copolymers and the carboxyvinyl polymers. These resins consist essentially of a colloidal water-soluble polyalkenyl polyether crosslinked polymer of acrylic acid crosslinked with a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with a polyallyl ether of sucrose.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 4,000, PEG 6,000 and PEG 10,000) also have gelling capacity and while they are considered as "additional polar solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface-Active Agent

The composition of the present invention further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agent and the weighted average of their HLB values is between about 9 and about 14. Yet, in other embodiments, when a water in oil emulsion is desirable, the composition contains one or more surface active agents, having an HLB value between about 2 and about 9.

Preferably, the composition of the present invention contains a non-ionic surfactant. Nonlimiting examples of possible non-ionic surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, and mono-, di- and tri-esters of sucrose with fatty acids (sucrose esters).

In certain case, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

Thus, in a preferred embodiment, the surface active agent, the composition contains a non-ionic surfactant, or a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In further embodiments, surface active agent comprises a combination of a non-ionic surfactant and an ionic surfactant, at a ratio of between 1:1 and 20:1.

The concentration of the surface active agent is between about 0.1% and about 5%.

Hydrophobic Solvent

Optionally, the foamable carrier further contains at least one hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers.

Foam Adjuvant

Optionally, a foam adjuvant is included in the foamable carriers of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Keratolytic Agent

In an embodiment of the present invention, the saccharide composition contains a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratiinization (such as psoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

Polar Solvent/Penetration Enhancer

In an embodiment of the present invention, the saccharide composition contains a polar solvent. In one or more embodiments, the polar solvent is a polyol, i.e., an organic substance that contains at least two hydroxy groups in its molecular structure. Examples of polyols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol, dibutylene glycol, glycerin, butane-1,2,3-triol, butane-1,2,4-triol and hexane-1,2,6-triol.

Additional polar solvents that can be contained in the composition of the present invention include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc) and alpha hydroxy acids, such as lactic acid, glycolic acid and polyethylene glycol. Notably, polar solvents, as exemplified above generally possess skin penetration enhancing properties.

Additional Components

In an embodiment of the present invention, a composition of the present invention includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, occlusive agents, oils, penetration enhancers, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment of the present invention, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment of the present invention, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof.

In an embodiment of the present invention, the additional component is a humectant. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, polyhydroxy alcohol, sorbitol, glycerol, hexanetriol, propylene glycol, butylene glycol, hexylene glycol, a hexylene glycol derivative, polyethylene glycol, a sugar, a starch, a sugar derivative, a starch derivative, alkoxylated glucose, hyaluronic acid, lactamide monoethanolamine, acetamide monoethanolamine and derivatives, esters, salts and mixtures thereof.

In an embodiment of the present invention, the additional component is a preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment of the present invention, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl) ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2- hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethyl-methacryl-ate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

Propellants

Examples of suitable propellants include volatile hydrocarbons such as butane, propane, isobutane and fluorocarbon gases, or mixtures thereof.

In certain embodiments, fluorohydrocarbon propellants, other than chloro-fluoro carbons (CMCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect of the invention are propellants made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

The propellant makes up about 5-25 wt % of the foamable composition. Aerosol propellants are used to generate and administer the foamable composition as a foam. The total composition including propellant, foamable compositions and optional ingredients is referred to as the foamable composition.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of at least one year, or preferably, at least two years at ambient temperature, as revealed in accelerated stability tests. Organic carriers and propellants tend to impair the stability of emulsions and to interfere with the formation of a stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The foam of the present invention has several advantages, when compared with hydroalcoholic foam compositions, such as described in WO 2004/071479:

(1) Breakability. The foam of the present invention is thermally stable. Unlike hydroalcoholic foam compositions of the prior art, the foam of the present invention is not "quick breaking", i.e., it does not readily collapse upon exposure to body temperature environment. Sheer-force breakability of the foam is clearly advantageous over thermally induced breakability, since it allows comfortable application and well directed administration to the target area.

(2) Skin drying and skin barrier function. short chain alcohols are known to dry the skin and impair the integrity of the skin barrier. By contrast, including a film forming agent in the composition of the present invention foes not cause unwanted skin barrier damage.

(3) Irritability. Due to the lack of alcohol and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Active Agents

In an embodiment of the present invention, an active agent in incorporated in the foamable saccharide composition.

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, wound healing agents and wart removers. As is known to one skilled in the art, in some instances a specific active agent may have more than one activity, function or effect.

Hygroscopic Property of the Composition

A hydroscopic substance is a substance that absorbs water readily from its surroundings. Microorganisms require water to grow and reproduce, and such water requirements are best defined in terms of water activity of the substrate. The water activity of a solution is expressed as $Aw=P/Po$, where P is the water vapor pressure of the solution and Po is the vapor pressure of pure water at the same temperature. Addition of a hygroscopic substance to an aqueous solution in which a microorganism is growing will have the effect of lowering the Aw, with a consequent effect upon cell growth. Every microorganism has a limiting Aw, below which it will not grow, e.g., for *streptococci*, *klebsiella* spp., *escherichia coli*, *clostridium perfringens*, and *pseudomonas* spp. the Aw value is 0.95. *Staphylococcus aureus* is most resistant and can proliferate with an Aw as low as 0.86.

The water activity of a product can be determined from the relative humidity of the air surrounding the sample when the air and the sample are at equilibrium. Measurement is performed by placing a sample in an enclosed space where this equilibrium can take place. Once this occurs, the water activity of the sample and the relative humidity of the air are equal. The measurement taken at equilibrium is called an equilibrium relative humidity or ERH. The relationship between the water activity and ERH is in accordance with the following formula:

$$Aw=ERH/100$$

Various types of water activity instruments are commercially available. One exemplary instrument uses chilled-mirror dewpoint technology while other instruments measure relative humidity with sensors that change electrical resistance or capacitance.

Saccharides have a great affinity for water, and as such, they exhibit hygroscopic properties; and the concentration of the saccharide determines the Aw of the carrier. As such, additions of saccharides to the composition can have a dramatic affect on Aw. In one or more embodiments, the saccharide is contained in the composition of the present invention at a sufficient concentration to provide an Aw value of the foamable composition of less than 0.9. In other embodiments, the concentration of the hygroscopic substance in the composition is selected to provide a Aw value selected from the ranges of (1) about 0.8 and about 0.9; (2) about 0.7 and about 0.8; and (3) less than about 0.7.

A saccharide composition having a water activity that is less than that which can support microbial growth can be used as topical treatment of superficial infectious conditions.

By providing a saccharide composition in a pressurized packaging this is isolated from the environment until immediately before use, the Aw of the composition is maintained. In comparison, other dosage forms such as solutions, creams, lotions, ointments and the like, involve repeated opening of the package closure, resulting in absorption of water from the surrounding environment and a subsequent elevation of the Aw (thus lowering the hygroscopicity of the product, and therefore decreasing its anti-infective potential). By contrast, a pressurized packaging does not allow for any humidity to be absorbed by the preparation, and therefore, the hygroscopic character of the composition cannot be damaged.

The Saccharide Composition as Carrier of an Anti-Infective Agent

In one or more embodiments, the saccharide composition of the present invention further contains an anti-infective agent, selected from the group of an antibiotic agent, an antibacterial agent, an antifungal agent, an agent that controls yeast, an antiviral agent and an antiparasitic agent. Combining the anti-infective effect of a saccharide composition, which acts through a dehydration mechanism, with an additional anti-infective agent that acts through alternate mechanisms results in a synergistic effect and consequently higher success rate of the treatment.

The terms "antibacterial" and "antibiotic" as used herein shall include, but are not limited to, any substance being destructive to or inhibiting the growth of bacteria or any substance having the capacity to inhibit the growth of or to destroy bacteria, and are used in the treatment of infectious diseases. In one or more embodiments, the antibiotic agent is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide, a naturally occurring antibiotic compound and analogs, derivatives, salts, ions and complexes thereof.

The terms "antifungal" as used herein shall include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, dermatophytosis, microsporum, trichophyton and epidermophyton infections, candidiasis, oral candidiasis (thrush), candidiasis of the skin and genital mucous membrane, candida paronychia, which inflicts the nail and nail bed and genital and vaginal candida, which inflict genitalia and the vagina. We have unexpectedly discovered that a saccharide composition containing an antifungal drug is more effective that other compositions, comprising the same concentration of the antifungal agent, which is not hygroscopic. Furthermore, we have discovered that an antifungal agent, which is known to be effective against dermatophites but not against candida, becomes effective against candida, when it is included in a saccharide composition, as described herein.

There is no particular limitation on the antifungal agents used in the compositions of this invention. By way of example, preferred suitable antifungal agents be made of polyenes, e.g., natamycin, nystatin; allylamines, e.g., naftifine, terbinafine; imidazoles, e.g., bifonazole, clotrimazole, econazole, fenticonazole, ketoconazole, miconazole, oxiconazole; diazole, triazoles, e.g., fluconazole, itraconazole, terconazole, tolnaftate, ciclopirox, undecylenic acid, sulbentine, griseofulvin, Amphotericin B, flucytosine (5FC), and morpholines, e.g., amorolfine, and the related morpholines and analogs, derivatives and salts thereof, and any combination thereof at a therapeutically effective concentration.

Any known antiviral agent, in a therapeutically effective concentration, can be incorporated in the foam composition according to one or more embodiments of the present invention.

Thus, in preferred embodiments of the present invention a pharmaceutical composition is provided, including:

(i) a saccharide aqueous solution;

(ii) about 0.2% to about 5% by weight of a surface-active agent;

(iii) about 0.01% to about 5% by weight of at least one polymeric agent selected from a bioadhesive agent, a gelling agent, a film forming agent and a phase change agent;

(iv) a therapeutically effective concentration of an anti-infective agent; and (v) a liquefied or compressed gas propellant at a concentration of about 3% to about 25% by weight of the total composition.

In one or more embodiments, the pharmaceutical composition further contains a penetration enhancer.

Fields of Applications

The foamable carrier of the present invention is suitable for treating any infected surface. In one or more embodiments, foamable carrier is suitable for administration to the skin, a body surface, a body cavity or mucosal surface, e.g., the mucosa of the nasal cavity, the mouth, the eye, the ear canal, the vagina and the rectum (severally and interchangeably termed herein "target site").

By selecting a suitable active agent, or a combination of at least two active agents, the foamable composition of the present invention is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present invention is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present invention, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present invention, the composition is useful for the treatment of wound, ulcer and burn. This use is particularly important since the composition of the present invention creates a thin, semi-occlusive layer, which coats the damaged tissue, while allowing exudates to be released from the tissue.

The composition of the present invention is also suitable for administering a hormone to the skin or to a mucosal membrane or to a body cavity, in order to deliver the hormone into the tissue of the target organ, in any disorder that responds to treatment with a hormone.

The invention is described with reference to the following examples. This invention is not limited to these examples and experiments. Many variations will suggest themselves and are within the full intended scope of the appended claims.

EXAMPLE 1

Foamable Saccharide Composition Containing Sorbitol and Honey

|  | SOR1 % w/w | SOR2 % w/w | HON1 % w/w |
|---|---|---|---|
| Sorbitol 70% | 89.50 | 89.50 | — |
| Honey | — | — | 89.50 |
| Steareth 2 | 2.00 | — | — |
| Ceteth 2 | — | 2.00 | 2.00 |
| Hydroxyethylcellulose | 0.50 | 0.50 | 0.50 |
| Propellant | 8.00 | 8.00 | 8.00 |
| Foam quality | G | G | G |

Upon release from the aerosol can a foam of Excellent quality (very small bubble size) is formed. The foam is stable when placed on the skin. Upon easy rubbing, the foam readily spreads on the skin and is rapidly absorbed.

EXAMPLE 2

Foamable Saccharide Comparison Containing Active Agents

The following active agents have been incorporated into Formulations SOR1, SOR2 and HON1:

Terbinafine 2%;

Miconazole 1%;

Iodine-povidone 5%;

Hydrocortisone acetate 0.1%;

Clobetasol dipropionate 0.05%; and

Clindamycin 1%

EXAMPLE 3

Usability Study: Comparison Between a Foam According to the Present Invention and an Ointment Product The objective of this study was to assess the usability properties of foam product "SOR1", in comparison with a comparator ointment. The study panelists (n=12) were asked to test the usability of two foam products, in comparison with a comparator ointment, with regard to the following parameters:

Ease of application
Uniform spreading
Accurate location
Skin absorption
Oily residue
Shiny residual look
Stickiness The panelists were instructed to rate a series of usability parameters and to grade each of the foam products according to the following scale:

Score −3: Ointment is much better than the foam (Ointment>>>Foam)

Score −2: Ointment is better than the foam (Ointment>>Foam).

Score −1: Ointment is slightly better than the foam (Ointment>Foam).

Score 0: Foam as good as Ointment (Foam=Ointment)

Score +1: Foam is slightly better than the Ointment (Foam>Ointment).

Score +2: Foam is better than the Ointment (Foam>>Ointment)

Score +3: Foam is much better than the Ointment (Foam>>>Ointment).

The mean result of the comparison indicated high preference to the foam in all usability parameters, as shown in the following table:

|  | Mean score |
|---|---|
| Ease of application | 1.4 |
| Uniform spreading | 0.8 |
| Accurate location | 0.3 |
| Skin absorption | 2.4 |
| Oily residue | 1.2 |
| Shiny residual look | 1.2 |
| Stickiness | 1.1 |

The invention claimed is:

1. A foamable saccharide composition for topical administration to the skin or vaginal body cavity including:
   (i) water;
   (ii) about 50% to about 80% by weight of a saccharide selected from the group consisting of a monosaccharide, a disaccharide, an oligosaccharide, a sugar alcohol and mixtures thereof; or honey, in an amount that provides about 50% to about 80% by weight of a mixture of saccharides in the composition;
   (iii) about 0.2% to about 5% by weight of a surface-active agent;
   (iv) about 0.01% to about 5% by weight of at least one polymeric agent selected from a bioadhesive agent, a gelling agent, a film forming agent and phase change agent; and
   (v) a foam adjuvant, the foam adjuvant comprising a fatty alcohol or a fatty acid, or a mixture thereof; and
   a liquefied hydrocarbon propellant or compressed gas propellant at a concentration of about 3% to about 25% of the total composition;
   wherein the saccharide composition is hygroscopic; and wherein the composition forms a breakable foam upon dispensing.

2. The saccharide composition of claim 1, further containing a hydrophobic solvent.

3. The saccharide composition of claim 2, wherein the composition is in the form of an oil in water emulsion.

4. The saccharide composition of claim 2, wherein the composition is in the form of a water in oil emulsion.

5. The saccharide composition of claim 1, further containing an additive selected from the group of a keratolytic agent and a polar solvent.

6. The saccharide composition of claim 1, further containing at least one active agent selected from the group of an active herbal extract, an acaricide, an age spot and keratose removing agent, an allergen, an analgesic agent, a local anesthetic, an antiacne agent, an antiallergic agent, an antiaging agent, an antibacterial agent, an antibiotic agent, an antiburn agent, an anticancer agent, an antidandruff agent, an antidepressant, an antidermatitis agent, an antiedemic agent, an antihistamine, an antihyperkeratolyte agent, an antiinflammatory agent, an antiirritant, an antilipemic agent, an antimicrobial agent, an antimycotic agent, an antiproliferative agent, an antioxidant, an anti-wrinkle agent, an antipruritic agent, an antipsoriatic agent, an antirosacea agent, an antiseborrheic agent, an antiseptic agent, an antiswelling agent, an antiviral agent, an antiyeast agent, an astringent, a topical cardiovascular agent, a chemotherapeutic agent, a corticosteroid, a dicarboxylic acid, a disinfectant, a fungicide, a hair growth regulator, a hormone, a hydroxy acid, an immunosuppressant, an immunoregulating agent, an insecticide, an insect repellent, a keratolytic agent, a lactam, a metal, a metal oxide, a mitocide, a neuropeptide, a non-steroidal anti-inflammatory agent, an oxidizing agent, a pediculicide, a photodynamic therapy agent, a retinoid, a scabicide, a self tanning agent, a skin whitening agent, a vasoconstrictor, a vasodilator, a vitamin, a vitamin D derivative, a wound healing agent and a wart remover.

7. The saccharide composition of claim 1, wherein the concentration of the saccharide is sufficient to provide a Aw value less than 0.9 or about 0.9.

8. The saccharide composition of claim 1, further containing a therapeutically effective concentration of an anti-infective agent.

9. The saccharide composition of claim 8, wherein the anti-infective agent is selected from the group consisting of an antibiotic agent, an antibacterial agent, an antifungal agent, an agent that controls yeast, an antiviral agent and an antiparasitic agent.

10. The saccharide composition of claim 9, wherein the antibiotic agent is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a cationic antimicrobial agent, a quaternary ammonium compound, a biguanide, chlorohexidine, a triguanide, a bisbiguanide, a polymeric biguanide, a naturally occurring antibiotic compound and salts, ions and complexes thereof.

11. The saccharide composition of claim 9, wherein the antifungal agent is useful in the treatment of an infection of dermatophytosis, microsporum, trichophyton and epidermophyton infections, candidiasis, oral candidiasis (thrush), yeast and candida.

12. The saccharide composition of claim 9, wherein the antifungal agent is selected from the group consisting of a polyene, natamycin, nystatin; an allylamine, naftifine, terbinafine; an imidazole, bifonazole, clotrimazole, econazole, fenticonazole, ketoconazole, miconazole, oxiconazole; a diazole, a triazoles, fluconazole, itraconazole, terconazole, tolnaftate, ciclopirox, undecylenic acid, sulbentine, griseofulvin, Amphotericin B, flucytosine (5FC), a morpholine compound, amorolfine, and the related morpholines and salts thereof, and any combination thereof at a therapeutically effective concentration.

13. The saccharide composition of claim 5, wherein the keratolytic agent is selected from the group consisting of urea, an alpha-hydroxy acid, lactic acid, phenol, resorcinol, salicylic acid, a keratolytic enzyme, a proteolytic enzyme and papain.

14. A method of treatment of a disorder of a target site comprising:
   administering to a target site in need of treatment, said target site selected from the group consisting of the skin, a body surface, a body cavity or mucosal surface, the nasal cavity, the mouth, the eye, the ear canal, the vagina and the rectum;
   a saccharide composition comprising:
      (i) water;
      (ii) about 50% to about 80% by weight of a saccharide selected from the group consisting of a monosaccharide, a disaccharide, an oligosaccharide, a sugar alcohol and mixtures thereof; or honey, in an amount that provides about 50% to about 80% by weight of a mixture of saccharides in the composition;
      (iii) about 0.2% to about 5% by weight of a surface-active agent;
      (iv) about 0.01% to about 5% by weight of at least one polymeric agent selected from a bio-adhesive agent, a gelling agent, a film forming agent and a phase change agent; and
      (v) a foam adjuvant, the foam adjuvant comprising a fatty alcohol or a fatty acid, or a mixture thereof; and
   a liquefied hydrocarbon propellant or compressed gas propellant at a concentration of about 3% to about 25% of the total composition;
   wherein the saccharide composition is hygroscopic; and wherein the composition forms a breakable foam upon administration.

15. The method of claim 14, wherein the disorder comprises an infection.

16. The method of claim 15, wherein the infection is selected from the group consisting of a bacterial infection, a fungal infection, a yeast infection, a viral infection and a parasitic infection.

17. The method of claim 14, wherein the disorder is selected from the group consisting of wound, ulcer and burn.

18. The method of claim 14, wherein the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, vitiligo, chlamydia infection, gonorrhea infection, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

19. The saccharide composition of claim 7, wherein the concentration of the saccharide is selected to provide a Aw value less than 0.7 or about 0.7.

20. The saccharide composition of claim 1 wherein the HLB of the surface-active agent is between about 2 and about 9.

21. The saccharide composition of claim 1, wherein the HLB of the surface-active agent is between about 9 and about 14.

22. The saccharide composition of claim 1, wherein the composition has an Aw value of less than 0.9 or about 0.9.

23. A foamable saccharide composition for topical administration comprising:
(i) water;
(ii) about 50% to about 80% by weight of a saccharide selected from the group consisting of a monosaccharide, a disaccharide, an oligosaccharide, a sugar alcohol and mixtures thereof; or honey in an amount that provides about 50% to about 80% by weight of a mixture of saccharides in the composition;
(iii) about 0.2% to about 5% by weight of a surface-active agent; and
(iv) a liquefied hydrocarbon propellant or compressed gas propellant at a concentration of about 3% to about 25% of the total composition,
wherein the saccharide composition is hygroscopic; and wherein the composition forms a breakable foam upon dispensing.

24. A foamable saccharide composition for topical administration including:
(i) water;
(ii) about 50% to about 80% by weight of a saccharide selected from the group consisting of a monosaccharide, a disaccharide, an oligosaccharide, a sugar alcohol and mixtures thereof; or honey in an amount that provides about 50% to about 80% by weight of a mixture of saccharides in the composition;
(iii) about 0.2% to about 5% by weight of a surface-active agent; and
(iv) a liquefied hydrocarbon propellant or compressed gas propellant at a concentration of about 3% to about 25% of the total composition,
wherein the foam is capable of providing an Aw value of less than about 9; and wherein the foam forms a breakable foam upon dispensing.

25. A method for delivering a saccharide composition, comprising
(a) charging a container with a composition comprising a foamable carrier and a liquefied or compressed gas hydrocarbon propellant, wherein the propellant is present at a concentration of about 3% to about 25% by weight of the total composition, and wherein the carrier comprises
(i) water;
(ii) about 50% to about 80% by weight of a saccharide selected from the group consisting of a monosaccharide, a disaccharide, an oligosaccharide, a sugar alcohol and mixtures thereof;
(iii) optionally honey, in an amount that provides about 50% to about 80% by weight of a mixture of saccharides in the composition;
(iv) about 0.2% to about 5% by weight of a surface-active agent;
(v) about 0.01% to about 5% by weight of at least one polymeric agent selected from a bioadhesive agent, a gelling agent, a film forming agent and a phase change agent; and
(vi) a foam adjuvant, the foam adjuvant comprising a fatty alcohol or a fatty acid, or a mixture thereof; and
(b) dispensing the composition onto a body surface or in a body cavity, wherein the composition is dispensed as a breakable foam.

26. The method of claim 25, wherein the breakable foam creates a semi-occlusive layer on the surface or body cavity.

27. A foamable composition for topical administration to the skin or vaginal body cavity including:
(i) water;
(ii) about 50% to about 80% by weight of a sugar alcohol;
(iii) about 0.2% to about 5% by weight of a surface-active agent;
(iv) about 0.01% to about 5% by weight of at least one polymeric agent selected from a bioadhesive agent, a gelling agent, a film forming agent and phase change agent; and
(v) a liquefied hydrocarbon propellant or compressed gas propellant at a concentration of about 3% to about 25% of the total composition, and
wherein the saccharide composition is hygroscopic; and wherein the composition forms a breakable foam upon dispensing.

28. The foamable composition of claim 27, further comprising a foam adjuvant, the foam adjuvant comprising a fatty alcohol or a fatty acid, or a mixture thereof.

* * * * *